United States Patent
Tanaami et al.

(10) Patent No.: US 6,873,410 B2
(45) Date of Patent: Mar. 29, 2005

(54) BIOCHIP READER

(75) Inventors: Takeo Tanaami, Musashino (JP); Yumiko Sugiyama, Musashino (JP)

(73) Assignee: Yokogawa Electric Corporation, Tokyo (JP)

( * ) Notice: Subject to any disclaimer, the term of this patent is extended or adjusted under 35 U.S.C. 154(b) by 0 days.

(21) Appl. No.: 10/664,908

(22) Filed: Sep. 22, 2003

(65) Prior Publication Data

US 2004/0057048 A1 Mar. 25, 2004

Related U.S. Application Data

(62) Division of application No. 10/098,534, filed on Mar. 18, 2002.

(30) Foreign Application Priority Data

| May 10, 2001 | (JP) | ......................................... 2001-139678 |
| May 10, 2001 | (JP) | ......................................... 2001-140137 |
| May 11, 2001 | (JP) | ......................................... 2001-140835 |
| Feb. 8, 2002 | (JP) | ............................................ 2002-31668 |

(51) Int. Cl.[7] .............................................. G01N 21/64
(52) U.S. Cl. ...................... 356/317; 356/417; 250/458.1
(58) Field of Search ................................. 356/317, 318, 356/417; 250/458.1, 459.1, 461.1, 461.2

(56) References Cited

U.S. PATENT DOCUMENTS 3,973,827 A * 8/1976 Uetake ........................ 359/355
6,262,423 B1 * 7/2001 Hell et al. ................ 250/458.1
6,345,115 B1 * 2/2002 Ramm et al. ................ 382/133
6,355,934 B1 * 3/2002 Osgood et al. .......... 250/458.1
6,494,373 B2   12/2002 Tanaami et al.
6,628,385 B1 * 9/2003 Osipchuk et al. ............ 356/318
2001/0046712 A1 * 11/2001 Hang et al. .................. 436/172

FOREIGN PATENT DOCUMENTS

| JP | 2001-002264 | 1/2001 |
| JP | 2001-74657  | * 3/2001 |

OTHER PUBLICATIONS

*New Optical Microscopes*, vol. II, Gahusai Kikaku Co., Ltd. pp. 132–133 (Mar. 28, 1995), English language translation of marked–up portions only, please see p. 1 in the spec.)

*GFP and Bio–imaging*, Yodosha Co., Ltd. pp. 158 (Oct. 25, 2000), (English language translation of marked–up portion only, please see pp. 2–3 in the spec.).

* cited by examiner

*Primary Examiner*—F. L. Evans
(74) *Attorney, Agent, or Firm*—Westerman, Hattori, Daniels & Adrian, LLP

(57) ABSTRACT

The present invention provides a biochip reader for reading with a detector the fluorescence image information from genes to which fluorescent substances are stuck and which are poured into biochip cells, by emitting coherent light beams such as laser light onto the cells as excitation light. The present invention aims to achieve a biochip reader that is small, cheap, and highly durable.

2 Claims, 10 Drawing Sheets

US 6,873,410 B2

BIOCHIP READER

This application is a divisional of prior application Ser. No. 10/098,534, filed Mar. 18, 2002.

BACKGROUND OF THE INVENTION

1. Field of the Invention

The present invention relates to a biochip reader and, in particular, to a biochip reader using light from a coherent source such as laser as excitation light.

2. Description of the Prior Art

FIG. 1 is a schematic view illustrating the principle and configuration of a biochip reader. This figure is based on the confocal optical system, mentioned on pages 132 and 133 of "Application of confocal laser microscopes to medicine and biology," New Optical Microscopes, Vol. II, published by Gakusai Kikaku (which means "Interdisciplinary Planning") Co., Ltd. on Mar. 28, 1995. In a biochip reader based on such a schematic view illustrating its principle and configuration, laser light from light source 1 emitted through pinholes provided in pinhole plate 2 is incident to objective lens 5 after being collimated by lens 3 and transmitted through dichroic mirror 4. Objective lens 5 condenses this excitation light and irradiates sample (biochip) 6.

The fluorescent substances stuck to genes on biochip 6 emit fluorescence by being excited with excitation light. This fluorescence is reflected by dichroic mirror 4 after passing through objective lens 5 and then concentrated by condenser lens 7 and forms image on the plane of pinhole plate 8. These images are the fluorescence images of genes on sample 6 and are detected by detector 9.

To observe the fluorescence image of sample 6 surface (two-dimensional image), it is necessary to scan the sample 6 surface with excitation light. In this case, normally, the excitation light is not scanned but the stage on which sample 6 is placed (not shown in the figure) is scanned in the direction perpendicular to the optical axis (called stage scan).

In such a biochip reader, laser light is used as the light source because use of white light as a source causes a shortage of light quantity. In addition, employing the confocal type using pinholes not only prevents the detected image from being affected by dust stuck to the surface of sample 6, but also prevents speckle noise from being generated because the excitation light is emitted to the sample after being condensed.

However, in such conventional biochip readers, there are problems that adjustment or conditioning of pinholes is troublesome and also this raises its cost. Furthermore, it is disadvantageous that the stage is required to be durable because it is moved for scanning and thus the cost of the stage becomes high.

Next, FIG. 2 shows another example of a schematic view of a conventional biochip reader illustrating its principle and configuration. Such a principle is, for example, mentioned on page 158 of "GFP and Bio-imaging," Experimental Chair in Post-genome Age, No. 3, a separate volume of Experimental Medicine, published by Yodosha Co., Ltd. on Oct. 25, 2000.

In FIG. 2, excitation light from a parallel-light light source such as laser (not shown in the figure) is concentrated by condenser lens 7 and incident to objective lens 13 after being reflected by dichroic mirror 12. In this case, the excitation light forms an image in the position of focal length f of objective lens 13 and this image acts as the second source to be incident to objective lens 13.

Sample 6 is irradiated with the excitation light that has transmitted through objective lens 13. As a sample, for example, a DNA chip that contains DNA on a slide glass whose surface is flat, or the like is used. At each site 15 of the DNA chip, fluorescent substances with which the DNA is labeled emit fluorescence by being excited with excitation light. The fluorescence forms an image on detector 18 via the image forming optical system. In other words, the fluorescence is made parallel by objective lens 13 as shown with continuous lines, passes through dichroic mirror 12 and barrier filter 16, and is incident to lens 17. The image of sample 6 formed by lens 17 is detected by detector 18.

In this case, the behavior of the excitation light irradiating over the entire sample surface is as follows:

Excitation light reflected at the flat sample surface shown with broken lines (this excitation light is called the reflected excitation light or the return excitation light) is focused by objective lens 13 and focused in the position of focal length f of objective lens 13.

The excitation light is incident to detector 18 after passing through lens 17 whose intermediate image plane is set at this focal position.

In addition, the reflected excitation light is transmitted through dichroic mirror 12 and barrier filter 16 before passing through lens 17. Barrier filter 16 is formed to pass fluorescence but reject (attenuate) the reflected excitation light and thus the reflected excitation light mixed into detector 18 as background light is reduced by being passed through this barrier filter 16.

However, in such conventional microscopes, the reflected excitation light cannot be sufficiently reduced although it is attenuated with the barrier filter. Although background light must be reduced to approximately $10^{-9}$ of the fluorescence to be detected in the measurement of fluorescent molecules or the like, there is a problem that an attenuation factor (ratio of exit light intensity to incident light intensity) of only about $10^{-7}$ can be obtained in this reader. Thus, the attenuation is clearly not sufficient.

Further, FIG. 3 is a schematic view of the biochip reader using a microlens array system illustrating its principle and configuration, mentioned in the Japanese patent application No. 2001-2264 submitted by the applicant concerned. In FIG. 3, a plurality of microlenses ML is arranged on microlens array 21, and light that has passed through each microlens (excitation light) is emitted to sample 23 through dichroic mirror 22. Sample 23 is a biochip, into each of whose cells genes are poured, each cell being arranged at the same pitch as the above microlenses and thus spatially arranged so that excitation light from each microlens irradiates each cell respectively.

Fluorescent substances are stuck to each gene on the biochip and generate emission owing to irradiation of excitation light. The emitted fluorescence is reflected by dichroic mirror 22, incident to lens 25 through barrier filter 24, and forms an image on detector 26 (e.g. a camera). In such a manner, a fluorescence image of the biochip can be observed with camera 26.

In addition, barrier filter 24 acts to transmit fluorescence but reject excitation light, and thus the use of this filter can prevent the excitation light reflected by the surface of sample 23 from being incident to camera 26.

However, in such biochip readers, if shading (cone-shaped light intensity distribution) is included in excitation light from the light source, non-uniformity is generated in read data. To prevent this, it is suggested to make the ratio a of the minimum value of light intensity to its maximum value to be 10 to 20%, by making the amount of shading small using only a center portion of the above conical intensity distribution as shown in FIG. 3. However, there occurs another problem that much light is wasted (the light-utilizing efficiency deteriorates) because this method discards light in the peripheral portion.

Furthermore, if the expression of mRNA in a biochip is to be measured using cDNA, there are large differences in the amounts of expression, which causes problems such as cases where a 10- to 100-fold difference exists as shown in FIG. 4(b) between the expression (signal intensity) of gene A and that of gene B shown in FIG. 4(a). That is, if the amount of expression is to be measured precisely without giving any change, analog-to-digital converters and amplifiers used in the detector must have wide dynamic ranges and high accuracy, and so are expensive. This is a problem.

In addition, there is another problem that, although there is a method to measure the amount of expression several times by changing the gains of analog-to-digital converters and amplifiers, this method takes time for measurement, and dispersion in measured values and discoloring of biochips also increase.

SUMMARY OF THE INVENTION

The objective of the present invention is to solve the above problems and to provide a biochip reader that is small, cheap and highly durable.

Another objective of the present invention is to provide a biochip reader that can sufficiently attenuate the reflected excitation light that constitutes background light.

A further objective of the present invention is to provide a biochip reader that can raise the light-utilization efficiency and can measure samples with high accuracy even if cheap and moderately accurate analog-to-digital converters and amplifiers are used.

DESCRIPTION OF THE PREFERRED EMBODIMENTS

Figure 5:
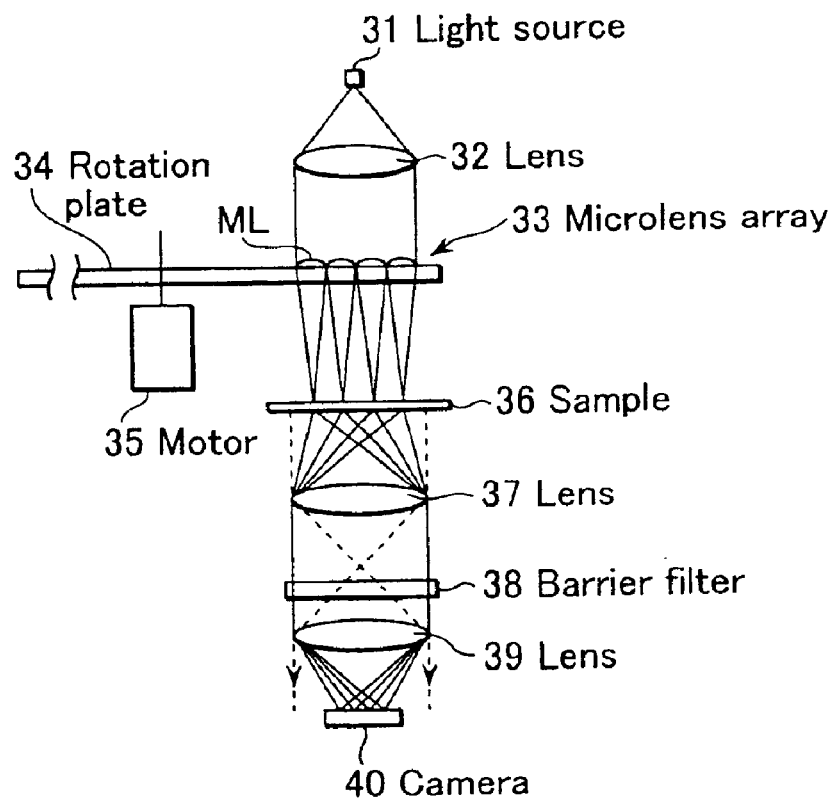
FIG. 5 shows a schematic view indicating the configuration of an essential part of an embodiment for a biochip reader based on the present invention.

The present invention will be described below in detail with reference to the drawings. FIG. 5 shows a schematic view indicating the configuration of an essential part of an embodiment for a biochip reader based on the present invention. In FIG. 5, numeral 31 shows a light source generating coherent light such as laser light (hereafter called "laser light") as excitation light, numeral 32 shows a lens converting the laser light into parallel light and numeral 33, a microlens array. Microlens array 33 is mounted on rotation plate 34 and composed of a plurality of microlenses ML arranged on that plate.

Numeral 35 shows a motor for rotating rotation plate 34, numeral 36 a sample, numeral 37 a lens, numeral 38 a barrier filter, numeral 39 a condenser lens, and numeral 40 a camera using CCDs or the like as detector elements.

Laser light emitted from light source 31 is changed to parallel light by lens 32 and is incident to microlens array 33. Each microlens ML irradiates sample 36 respectively by condensing laser light. Sample 36 has a construction in which a plurality of cells is arranged in a two-dimensional manner and genes are poured into each cell.

When rotation plate 34 is rotated with motor 35, excitation light beams focused with each microlens ML are scanned over sample 36. Microlenses ML are arranged on rotation plate 34, with the relation between spatial positions such that each excitation light beam can be scanned over each cell individually.

Fluorescence from each gene is incident to lens 39 through barrier filter 38 after being incident to lens 37. Barrier filter 38 acts to transmit fluorescence from sample 36 but reduces the incident excitation light passing through sample 36 and thus is used to reject background light for the sample image.

The sample image focused and formed by lens 39 is detected by detector elements (not shown in the figure) of camera 40.

Using such a configuration, a two-dimensional sample image can be easily obtained by producing multi-beams using a plurality of microlenses and by scanning samples with those beams.

In addition, it is not necessary to employ a confocal reader as required in conventional readers, because dust stuck to samples can be drastically reduced by using cartridges or the like. However, an adequate quantity of excitation light is required. In the present invention, since laser light is used as excitation light, a sufficient quantity of light at high luminance can be obtained.

Further, speckle noise is not generated in a sample image in the present invention, because the excitation light is focused with microlenses. Furthermore, since pinholes as in the case in conventional readers are not used, readers based on the present invention are easier to adjust. In addition, readers that are small, cheap and highly durable can be easily obtained because the moving mechanism to move a stage is not necessary.

Figure 6:
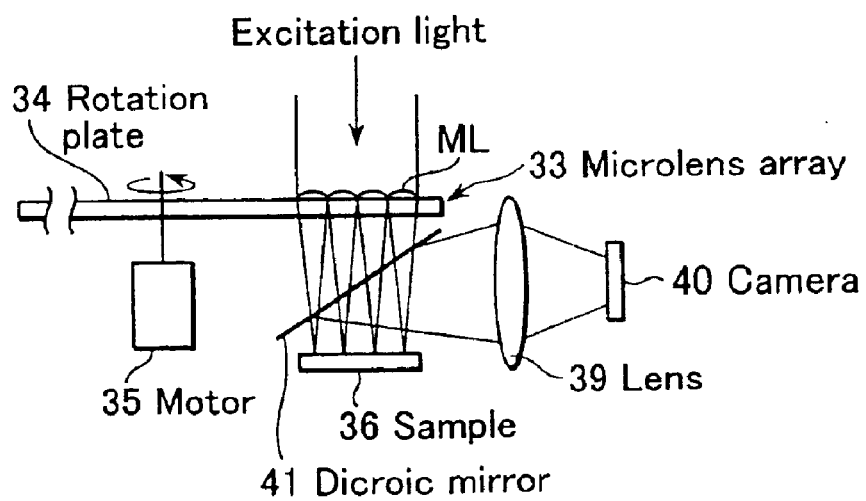
FIG. 6 shows a schematic view indicating the configuration of an essential part of another embodiment of the present invention.

FIG. 6 shows a schematic view indicating the configuration of an essential part of another embodiment of the present invention. Although the biochip reader shown in FIG. 5 is of the transmission type, the reader shown in FIG. 6 is of the reflection type. Dichroic mirror 41 is arranged between microlens array 33 and sample 36 and fluorescence emitted from sample 36 is reflected by this dichroic mirror 41 and incident to lens 39. Lens 39 condenses this fluorescence and forms an image on the detector element plane of camera 40. Other configurations and operations are the same as those shown in FIG. 5.

The above embodiments of the present invention have the following effects:
(1) Since excitation light beams irradiating each gene on a sample are focused with microlenses, speckle noise is not generated on observed images of the genes.
(2) There are fewer adjusting points than in conventional confocal biochip readers and thus fabrication is easier because the reader is not of the confocal type and so does not use pinholes.
(3) The reader does not require the stage on which a sample is placed for light scanning to be moved as in conventional readers. This facilitates the production of small, cheap, and highly durable biochip readers.

Figure 1:
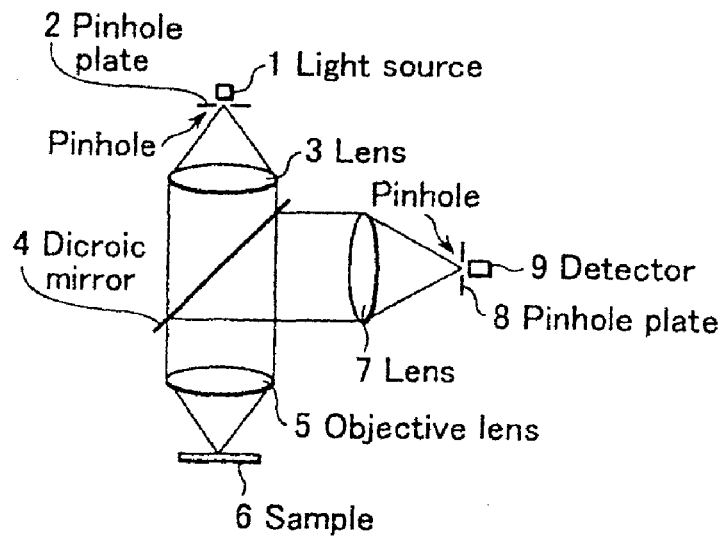
FIG. 1 is a schematic view of a conventional biochip reader illustrating its principle and configuration.
Figure 2:
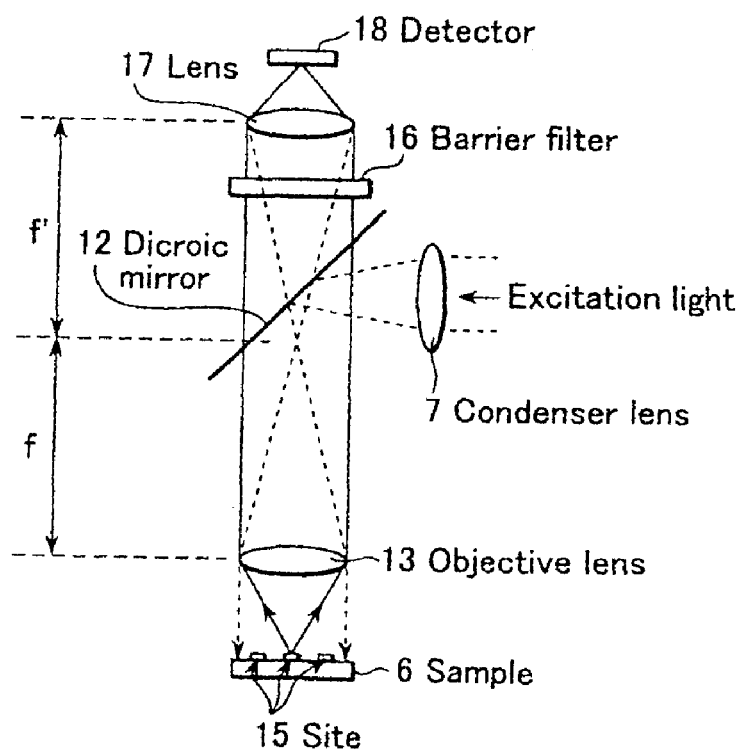
FIG. 2 shows another example of a schematic view of a conventional biochip reader illustrating its principle and configuration.
Figure 7:
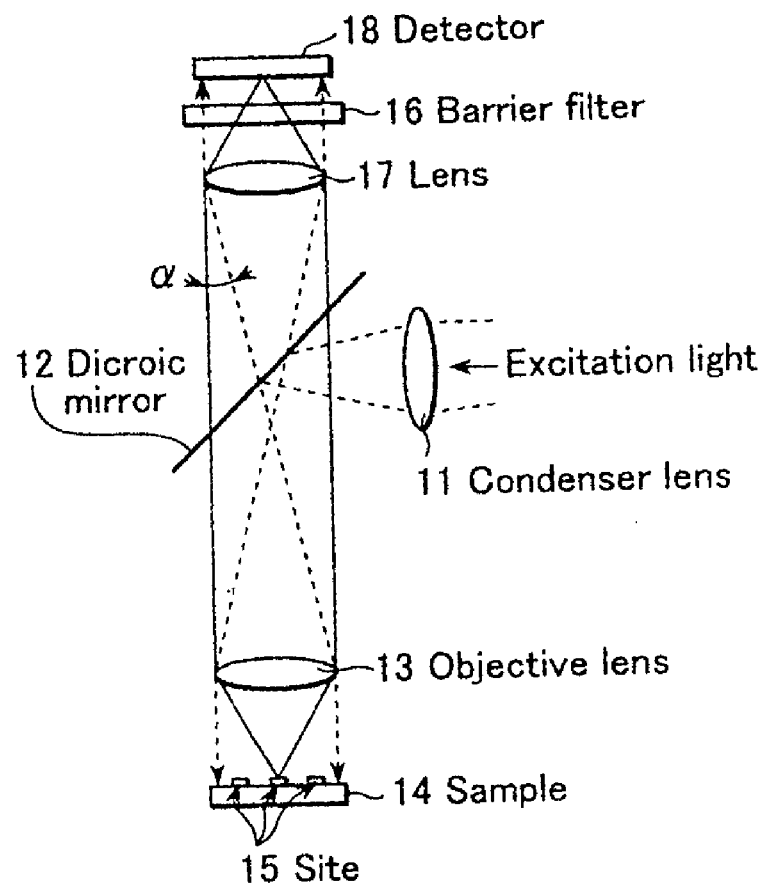
FIG. 7 shows a schematic view indicating the configuration of an essential part of the third embodiment of the present invention.
Figure 8:
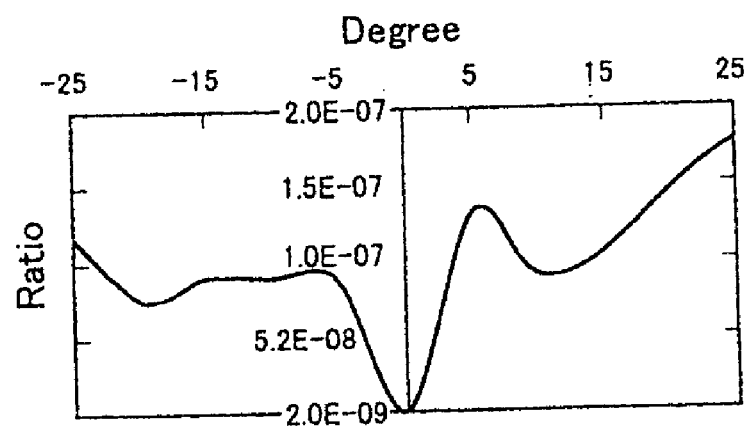
FIG. 8 is a graph indicating the attenuation factor characteristic of the barrier filter.

FIG. 7 shows another embodiment of the present invention, in which excitation light is incident to a barrier filter at the incident angle of ±5 degrees or less. The difference of this embodiment from the example of conventional ones shown in FIG. 2 is the arranged barrier filter position. In FIG. 7, barrier filter 16 is arranged between lens 17 and detector 18. The attenuation factor (ratio of exit light intensity to incident light intensity) of barrier filter 16 depends on the incident angle of light as shown in FIG. 8. In order to obtain the attenuation factor of $10^{-7}$ or better, it is necessary to suppress the incident angle to the barrier filter to ±5 degrees or less, while the data shown in FIG. 8 are example measurements for a barrier filter using parallel laser light. In general-purpose spectrophotometers, these values cannot be obtained because divergent or convergent light is used.

Such arrangement of barrier filter 16 attenuates the incident excitation light to a value of about $10^{-9}$ of the original incident light because the excitation light is incident to barrier filter 16 at an angle of ±5 degrees or less. For this reason, background light at an observed image on the surface of detector 18 is sufficiently little.

In addition, the present invention is not limited to the above embodiments. For example, configurations illustrated below may be employed.

Figure 9:
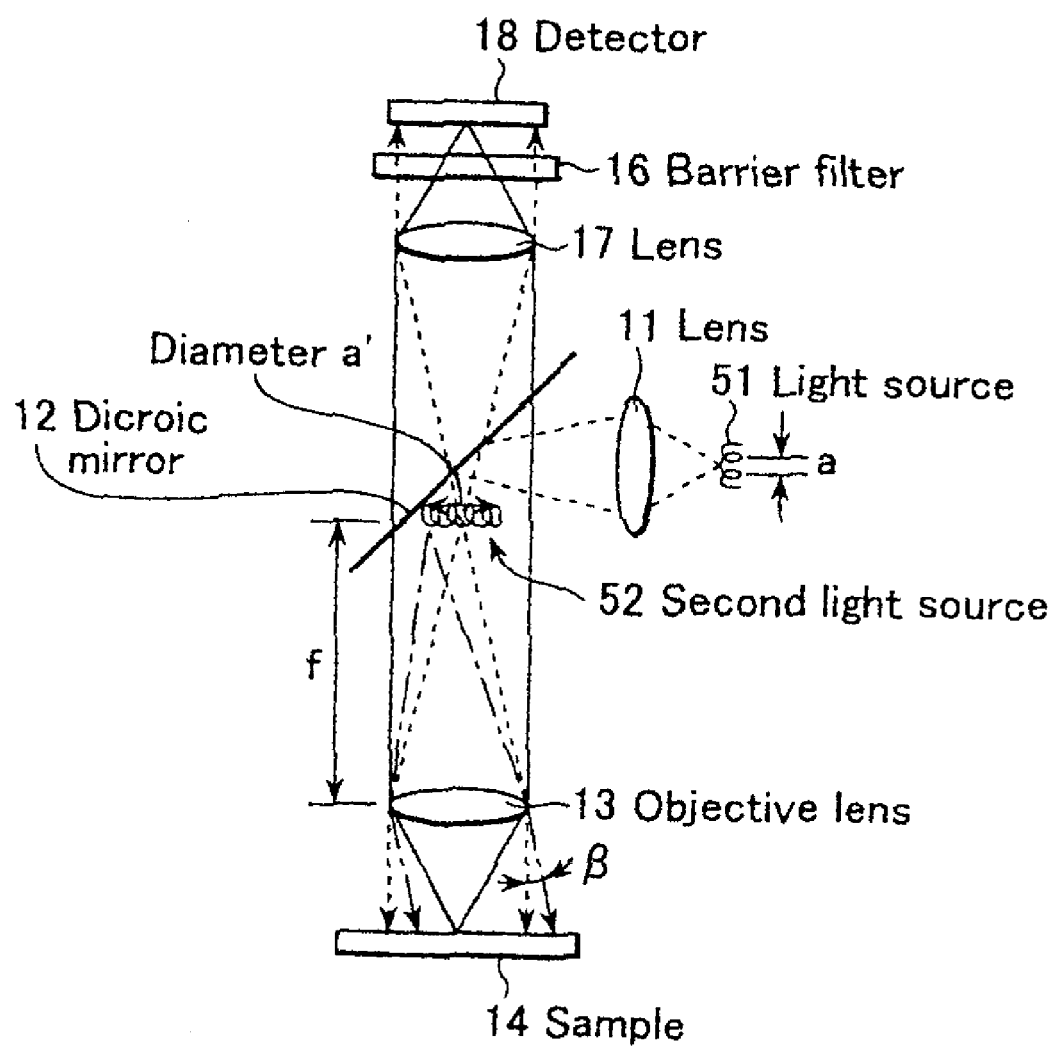
FIG. 9 shows a schematic view indicating the configuration of an essential part of another embodiment of a biochip reader based on the present invention.

(1) The Case Related to the Size of Light Source Image:

FIG. 9 shows a schematic view indicating the configuration of an essential part of Koehler's illumination system in the case where non-laser light such as white light is used. Light from light source 51 (diameter of light source is "a") forms second light source 52 having diameter a' by being incident to condenser lens 11. Sample 14 is irradiated by this second light source 52. The angle β of the angle of excitation light irradiating sample 14 in this case (this angle is called "irradiation angle") depends on the diameter of second light source 52.

In transmission type or reflection type microscopes, necessary and sufficient resolution cannot be obtained unless there is a large angle β in Koehler's illumination. Similarly, in fluorescence microscopes, the diameter a' of light source image 52 is expanded to about 10 times the diameter "a" of the original light source 51, enlarging the angle β.

However, since, when the angle β is made large, the incident angle to barrier filter 16 also becomes large and degrades the attenuation factor of excitation light, there is a limit for angle β. The following relationship exists between the light source image and the focal length f of objective lens 13:

$$a'/2 = f\beta$$

That is, $$\beta = a'/(2f)$$

where f is the focal length of objective lens 13.

In order to obtain a sufficient attenuation factor, it is necessary to suppress the angle β to ±5 degrees or less. To achieve this, for example, the size of the light source or the focal length f' of an optical system for excitation or the like may be adjusted.

Figure 10:
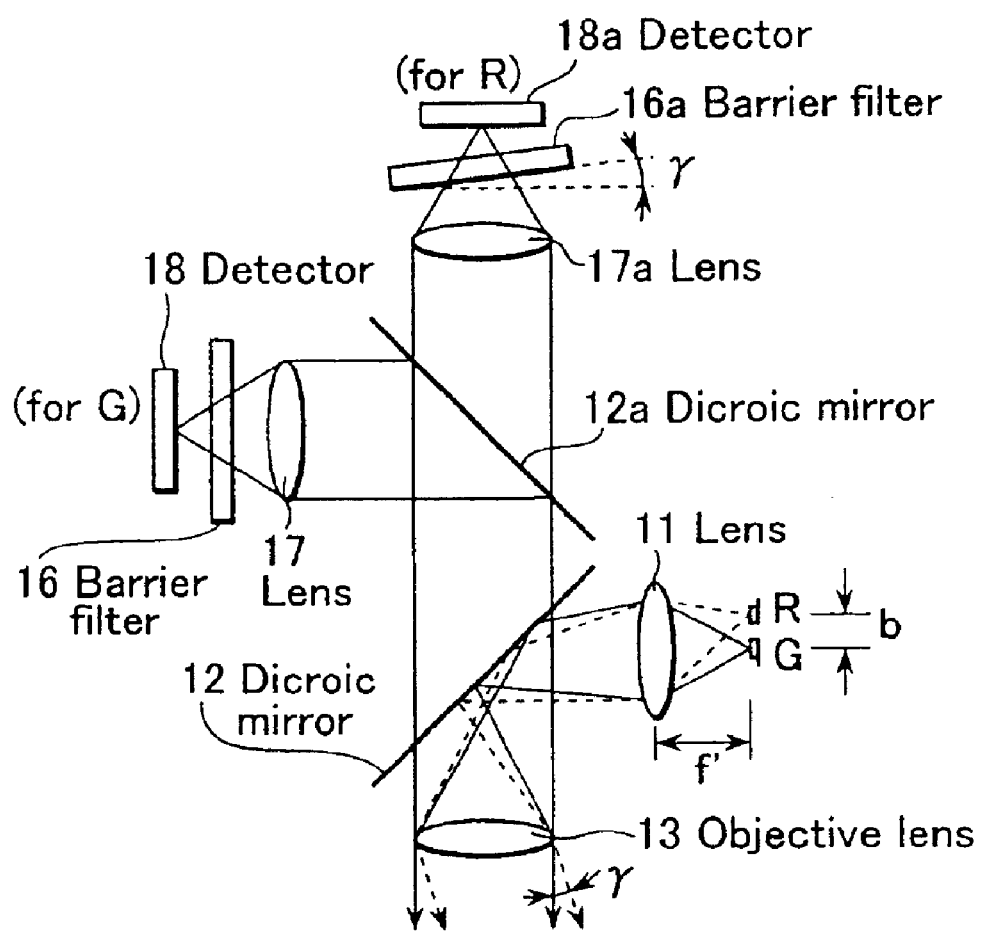
FIG. 10 shows a schematic view illustrating a biochip reader using a light source array.

(2) The Case of Light Source Array:

FIG. 10 shows a schematic view illustrating the configuration of the reader using a light source array composed of two different wavelength light sources such as green G and red R. The G light source is placed on the optical axis in a position f' apart from lens 11 and the R light source is placed in a place apart from the optical axis by b in that position. In such arrangement, light from the G light source is incident normal to the surface of a sample placed horizontally and light from the other R light source is incident to that surface at an irradiation angle of γ (=f'b).

The excitation light reflected at the sample surface is transmitted through objective lens 13 and dichroic mirror 12. Then, shorter wavelength light (on the G light source side) is reflected by second dichroic mirror 12a and the other longer wavelength light (on the R light source side) is transmitted through second dichroic mirror 12a.

The former forms an image on detector 18 via image-forming lens 17 and barrier filter 16 and the latter forms an image on detector 18a via image-forming lens 17a and barrier filter 16a.

In this case, if barrier filter 16a is mounted horizontally, reflected excitation light originated by the R light source is obliquely incident to the filter at an angle of γ. Accordingly, barrier filter 16a is arranged at angle γ oblique to the horizontal plane so that the excitation light is incident normal to the plane.

This makes it possible for the excitation light reflected from the sample surface to be incident normal to barrier filters 16 and 16a and thus both of the excitation lights are sufficiently attenuated.

Figure 11:
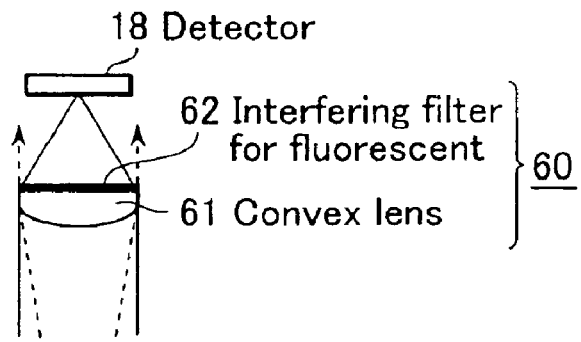
FIG. 11 shows a schematic view indicating another embodiment of an image-forming lens.

(3) Example of Version Related to Image-Forming Lens:

FIG. 11 shows a schematic view indicating the configuration of essential parts of an image-forming lens. This is an example for using a lens with a fluorescence filter 60 that has the barrier filter function together with the image-forming lens function.

This lens with a fluorescence filter 60 has a construction in which an interfering filter for fluorescence 62 is stuck to the flat side of convex lens 61, and attenuates the reflected excitation light with this interfering filter 62 like the barrier filter.

Figure 12:
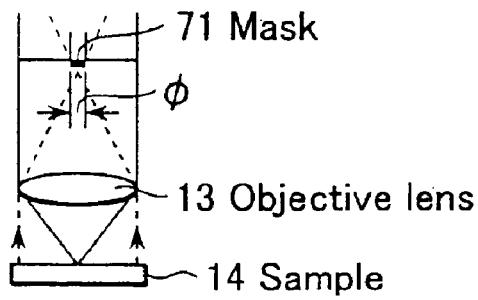
FIG. 12 shows a schematic view indicating a biochip reader using a mask.

(4) Example of Version for Changing to the Point Mask Type:

As shown in FIG. 12, the excitation light reflected from the sample is cut by placing mask 71 in the position where the excitation light is focused by objective lens 13. Mask 71 is, for example, supported with a transparent plate or three stays or the like radially extended in the horizontal direction. If the diameter φ of mask 71 is about 1.22 λ/NA, (in other words, if the opening of mask 71 has an area nearly equal to that for the diameter of the excitation light beam), the reflected excitation light can be cut by 80% or more. In this case, λ denotes the wavelength of excitation light and NA represents the Numerical Apertures for objective lens 13. The barrier filters used in the above embodiments need not be used. Otherwise, a cheap filter that has low attenuation factor may be used.

Figure 13:
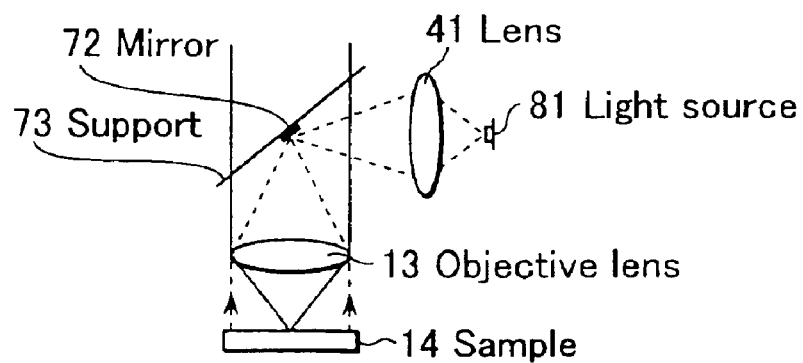
FIG. 13 shows a schematic view indicating a biochip reader configuration using a mirror.

(5) Example of Version for Changing to the Point Mirror Type:

In lieu of the dichroic mirror shown in the above embodiments, a small piece of mirror 72 can be placed in the position of the second light source in Koehler's illumination as shown in FIG. 13. This mirror 72 has an area nearly equal to that for the diameter of excitation light beam and reflects the excitation light from light source 81 like the dichroic mirror and irradiates sample 14. At the same time the mirror also reflects the reflected excitation light focused with objective lens 13 towards the light source. Accordingly, the reflected excitation light is not incident to the detector (not shown in the figure).

In addition, mirror 72 is held by support 73 composed of a transparent substrate or stays to keep its mounting position and angle.

Figure 14:
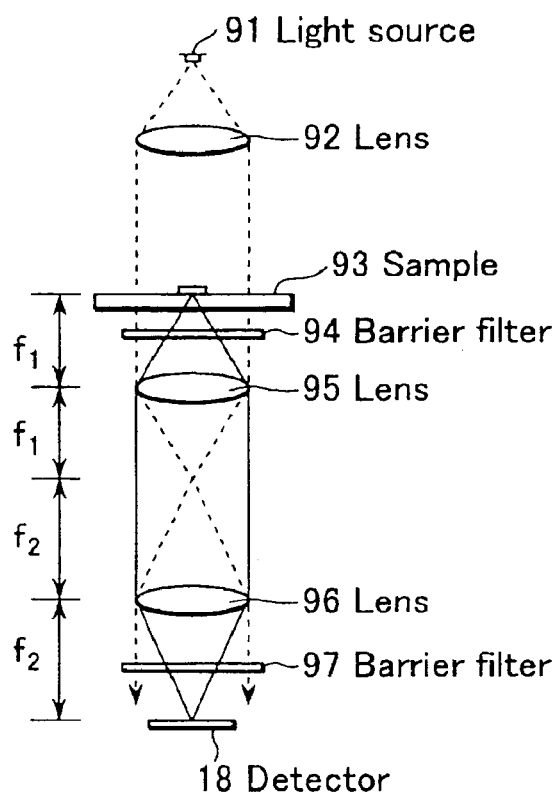
FIG. 14 shows a schematic view indicating the configuration of an embodiment for a transmission type biochip reader.

(6) The Case using a Transmission Type Fluorescence Reader:

FIG. 14 shows a schematic view indicating an embodiment for a transmission type fluorescence reader. In this case, the transmitted excitation light can also be attenuated using the barrier filter similarly. Barrier filters 94 and 97 are arranged between sample 93 and objective lens 95 and between image-forming lens 96 and detector 18 respectively. In this case, either of the barrier filters only may be employed.

In addition, objective lens 95 and image-forming lens 96 constitutes a telecentric system.

Figure 15:
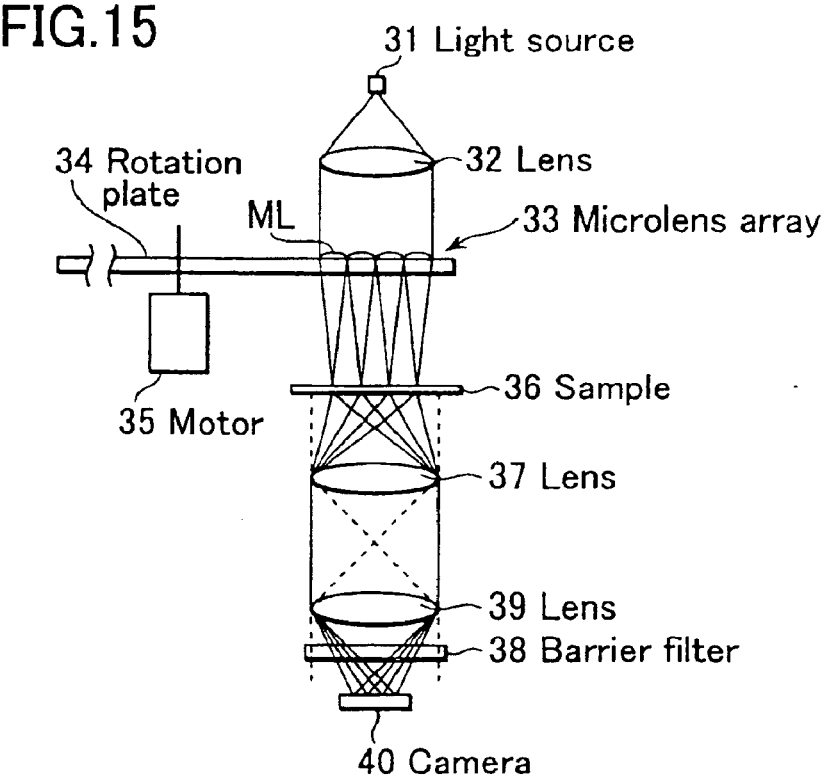
FIG. 15 shows a schematic view indicating the configuration of an essential part of another embodiment of the present invention.

FIG. 15 shows that barrier filter 38 is arranged between lens 39 and camera 40 in the configuration shown in FIG. 5. The excitation light transmitted through sample 36, as shown with dotted lines in FIG. 15, is incident to an image-forming optical system composed of lenses 37 and 39 as almost parallel light and then incident to camera 40 as almost parallel light.

In this case, the excitation light is incident to barrier filter 38 at an incident angle of ±5 degrees or less and is attenuated to $10^{-7}$ or less of the incident light.

According to these embodiments, the following effects can be recognized:

(1) The excitation light can easily be attenuated because the excitation light is devised to be incident to the barrier filter at an incident angle of ±5 degrees or less.

(2) Actions equivalent to using a barrier filter can easily be achieved without using a barrier filter by employing a convex lens as the image-forming lens and attaching an interfering filter for fluorescence to the convex lens.

(3) Mixing the reflected excitation light into the detector can easily be prevented without using the barrier filter because the reflected excitation light focused with the objective lens is masked or reflected.

(4) The excitation light to be incident to the detector can easily be attenuated by arranging the barrier filter(s) even in transmission-type fluorescence readers.

Figure 3:
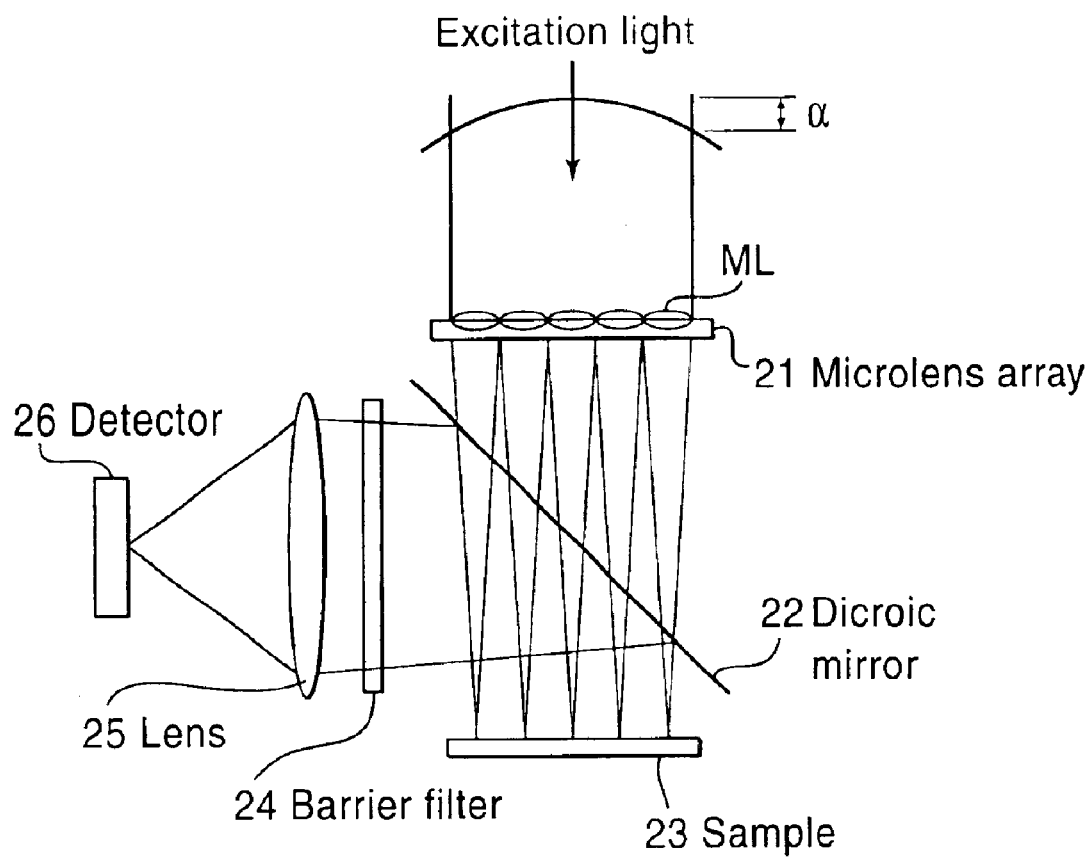
FIG. 3 shows the third example of a schematic view of a biochip reader illustrating its principle and configuration.
Figure 4A:
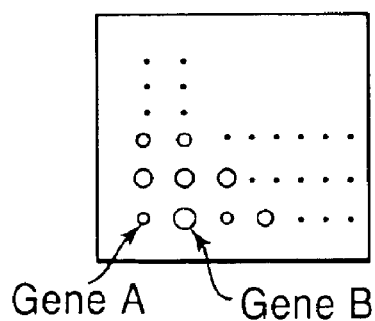
FIG. 4 is a drawing illustrating a biochip and a difference between the amounts of expression (signal intensities) for genes.
Figure 4B:
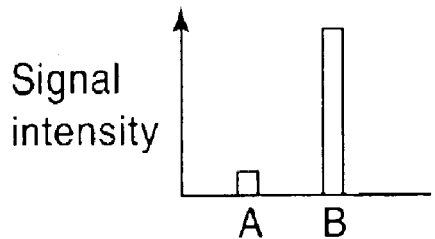
Figure 16:
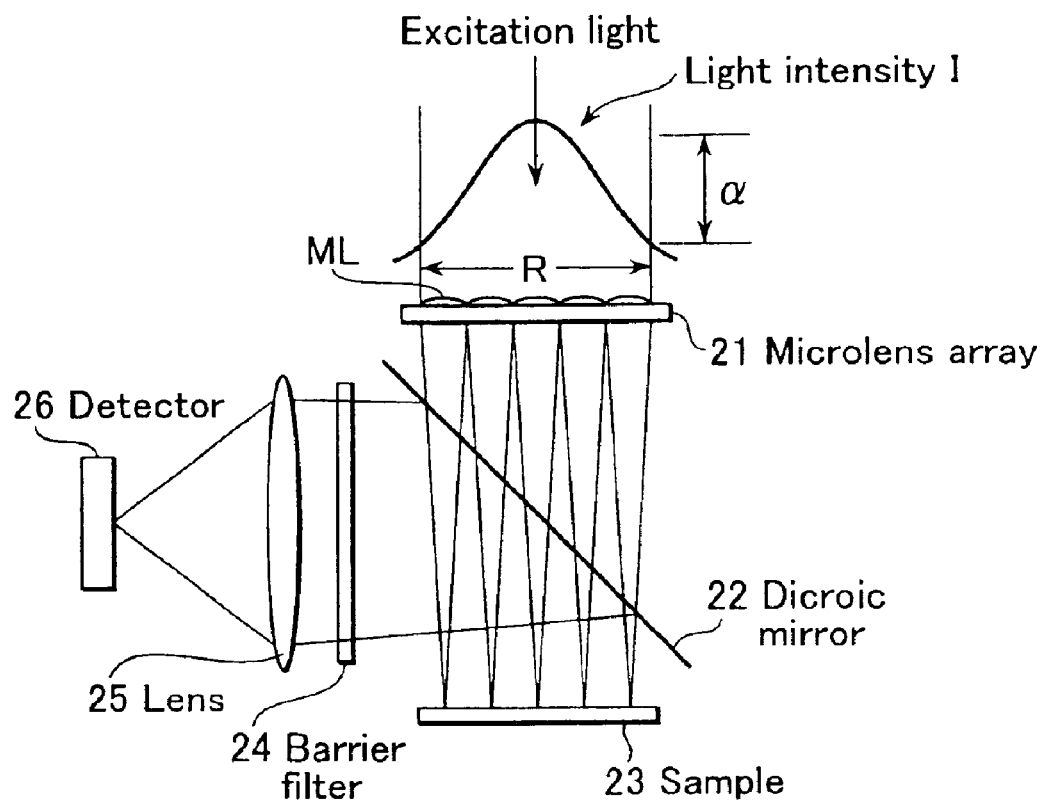
FIG. 16 shows a schematic view indicating the configuration of an essential part of the third embodiment of the present invention.

In addition, as a solution to the problems shown in FIG. 3 and FIGS. 4A and 4B, the following configuration should be adopted:

At the same time as generating excitation light composed of strong and weak light intensity parts from a light source, the excitation light is intentionally shaded to a significant extent. For example, as shown in FIG. 16, the excitation light is forced to have a light intensity pattern in which the intensity is strong at the center part and weak in the peripheral part. The light intensity pattern is arranged such that the ratio a of the lowest value to the highest value of light intensity I in the effective range R of that parallel light is about 90%. The excitation light having such a light intensity distribution irradiates sample 23 in the same light intensity pattern via microlens array 21 and dichroic mirror 22.

Figure 17:
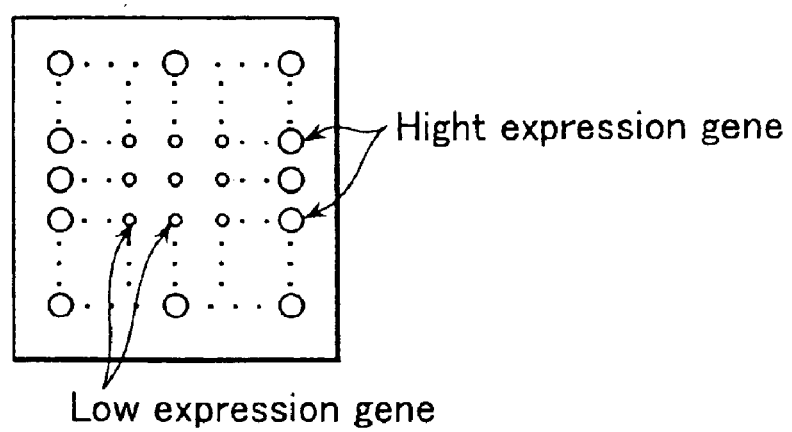
FIG. 17 is a drawing illustrating a condition of gene arrangement on a sample.

On the other hand, at sample 23, genes are arranged so that the expression distribution shows an inverted pattern from the intensity pattern of excitation light. This is done by arranging the genes with the higher expression genes placed in outer cells and the lower expression genes placed in inner cells, as shown in FIG. 17.

By placing the light intensity distribution of excitation light and the expression distribution of genes in a relationship as mentioned above, low and high expression genes, in other words, genes which produce little fluorescence or much fluorescence, are irradiated with strong and weak intensity excitation light respectively.

As a result, even if there is a great difference in expressions, the difference in the fluorescence from each gene to be incident to the detector is small. Accordingly, analog-to-digital converters and amplifiers that are cheap and have moderate accuracy can be used in the detector because wide dynamic ranges and high accuracy are not required.

Further, the excitation light distribution is separately measured in advance and fluorescence from the sample is used by being corrected using the excitation light distribution.

Figure 18:
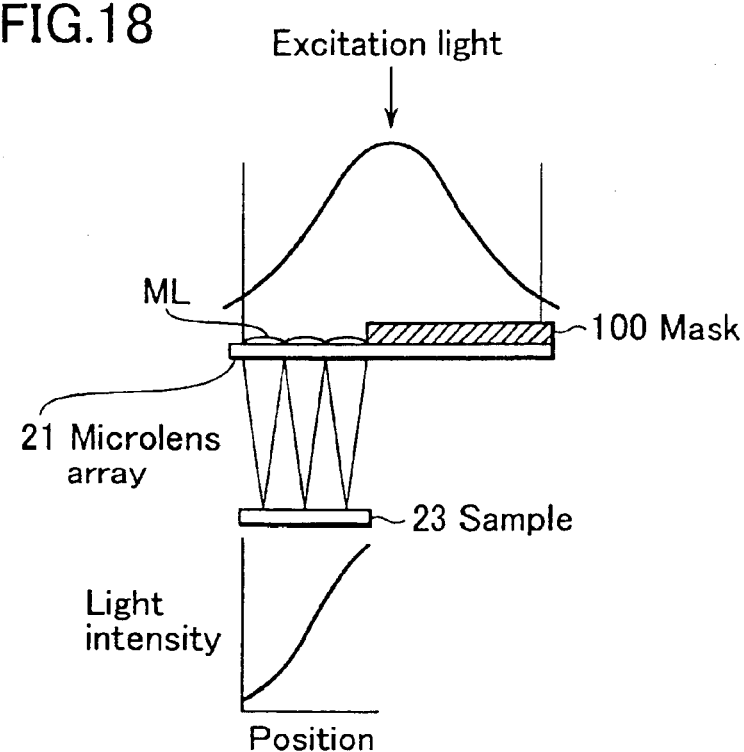
FIG. 18 shows a schematic view indicating the configuration of an essential part of the other embodiment of the present invention.

Furthermore, the present invention is not limited to the above embodiments. For example, if only a part of excitation light is employed using light cutting or light reducing mask 100 as shown in FIG. 18, the excitation light emitted to a biochip indicates the light intensity distribution shown in the figure. As described above, if a mask having the light cutting or light reducing pattern (also called "concentration pattern" here) is used, the degree of freedom in arranging genes on a biochip is greatly improved.

Figure 19:
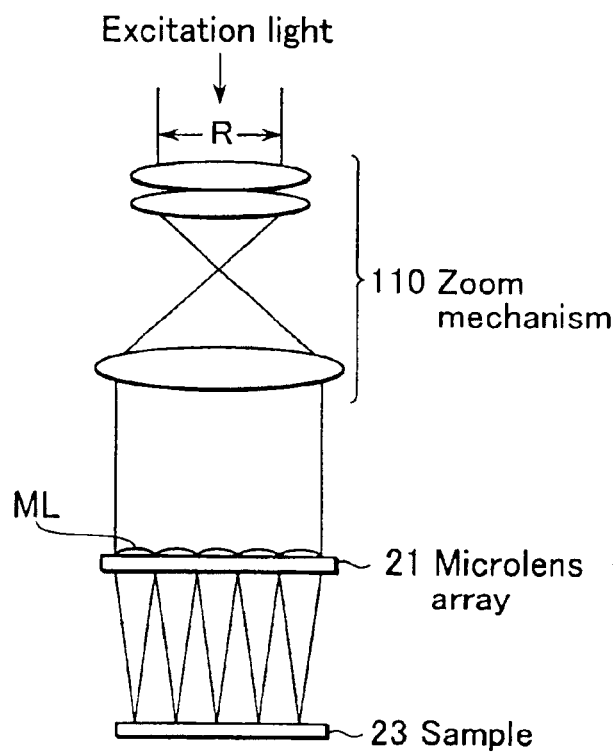
FIG. 19 shows a schematic view indicating the configuration of an essential part of the separate other embodiment of the present invention.

In addition, the reader can also be configured so as to make shading of excitation light variable as shown in FIG. 19. In FIG. 19, the difference of the configuration from that shown in FIG. 16 is the zoom mechanism. Zoom mechanism 110 uses ordinary zoom lenses and produces a parallel light beam from the light source (not shown in the figure) to microlens array 21 after suitably expanding or contracting the light beam.

If the beam is expanded with zoom mechanism 110, the light intensity distribution pattern of the excitation light emitted from the light source is extended transversely, and so the intensity distribution pattern of excitation light incident to microlens array 21 becomes flatter. On the contrary, if the light intensity distribution pattern is contracted, the incident excitation light distribution gives a steeper pattern.

Since shading varies with expansion or contraction as shown above, shading can be set arbitrarily corresponding to sample 23 by operating zoom mechanism 110.

Figure 20:
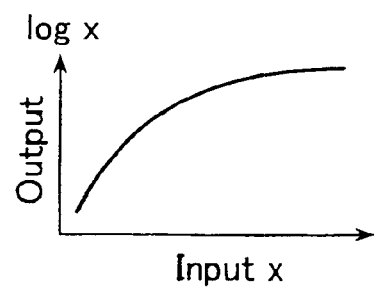
FIG. 20 is a graph showing the input-output characteristic of detector elements.

Further, a configuration to detect a fluorescence image using a detector composed of detector elements having input-output characteristics of a logarithmic relationship as shown in FIG. 20 may be used without changing the light intensity distribution of excitation light or the arrangement of sample genes.

According to such a configuration, even if there is a great difference in inputs (fluorescence quantities), saturation in analog-to-digital converters and amplifiers on the detector side can be prevented and so such converters and amplifiers do not need wide dynamic ranges and high accuracy.

In accordance with the invention having the embodiments described above, even if there are great differences in the expressions of each gene on a biochip, wide dynamic ranges and high accuracy are not required for detectors. Thus, satisfactory sample images can be detected with a detector using analog-to-digital converters and amplifiers that are cheap and have moderate accuracy.

Furthermore, since shading for light intensity distribution of the light source can be increased, obtaining a great increase in the efficiency of light quantity can also be intended.

What is claimed is:

1. A biochip reader comprising:

a light source to irradiate an excitation light beam to a sample;

an image-forming optical system to form an image of fluorescence generated from fluorescent substances in said sample irradiated by said excitation light beam;

a detector to read the image and;

a mask to prevent mixing of reflected excitation light into the detector, that has approximately the same area as that for a diameter of said excitation light beam and masks the excitation light beam focused with an objective lens in said image-forming optical system.

2. A biochip reader comprising:

a light source to irradiate an excitation light beam to a sample;

an image-forming optical system to form an image of fluorescence generated from fluorescent substances in said sample irradiated by said excitation light beam;

a detector to read the image and;

a mirror to prevent mixing of reflected excitation light into the detector side that has approximately the same area as that for a diameter of said excitation light beam and reflects the excitation light beam focused with an objective lens in said image-forming optical system.

* * * * *